United States Patent [19]
Herstein et al.

[11] Patent Number: 4,534,964
[45] Date of Patent: Aug. 13, 1985

[54] HAIR CONDITIONING SHAMPOO

[75] Inventors: Morris S. Herstein, Nanuet, N.Y.; Walter P. Smith, Sandy Hook; Geoffrey R. Hawkins, Branford, both of Conn.

[73] Assignee: Richardson-Vicks Inc., Wilton, Conn.

[21] Appl. No.: 569,528

[22] Filed: Jan. 12, 1984

Related U.S. Application Data

[63] Continuation-in-part of Ser. No. 433,565, Oct. 4, 1982, abandoned.

[51] Int. Cl.$^3$ .................. A61K 7/06; A61K 31/16; C11D 1/94
[52] U.S. Cl. .................. 424/70; 252/545; 514/873
[58] Field of Search .................. 424/70, 320, 329; 252/545

[56] References Cited

U.S. PATENT DOCUMENTS

| | | | |
|---|---|---|---|
| 3,766,267 | 3/1971 | Zak et al. | 424/320 X |
| 3,855,290 | 6/1973 | Zak et al. | 424/70 X |
| 4,075,131 | 9/1976 | Sterling | 424/70 X |
| 4,110,263 | 6/1977 | Lindemann et al. | 252/545 |
| 4,247,538 | 9/1978 | Barker | 424/70 |

Primary Examiner—Sidney Marantz
Assistant Examiner—Shawn P. Foley
Attorney, Agent, or Firm—Salvatore R. Conte

[57] ABSTRACT

An aqueous hair conditioning shampoo composition comprising about 0.5–10 percent by weight of cocamidopropyl hydroxysultaine and about 0.1–6 percent by weight of a quaternary halide of an N,N,N-trialkylaminoalkylene gluconamide.

6 Claims, No Drawings

HAIR CONDITIONING SHAMPOO

CROSS-REFERENCE TO RELATED APPLICATION

This application is a continuation-in-part of our co-pending application Ser. No. 433,565, filed Oct. 4, 1982, now abandoned.

FIELD OF THE INVENTION

This invention relates to improved cosmetics for use in hair treatment and, more particularly, to enhancing the cosmetic properties of hair conditioning shampoos containing cocamidopropyl hydroxysultaine by the inclusion of certain quaternary halides of an N,N,N-trialkylaminoalkylene gluconamide.

RELATED PRIOR ART

The quaternary halide salts of N,N,N-trialkylaminoalkylene gluconamide used in this invention are described in U.S. Pat. Nos. 3,766,267 and 3,855,290 for use as emollients in topical and cosmetic applications. Also see U.S. Pat. No. 4,247,538 and references therein cited for compositions useful for shampooing and conditioning hair wherein sultaine ($SO_3^-$) and betain ($COO^{31}$) amphoteric detergents, akin to cocamidopropyl hydroxysultaine, are utilized.

BACKGROUND OF THE INVENTION

Cocamidopropyl hydroxysultaine, also known chemically as 3-[(3-cocoamidopropyl)dimethylammonio]-2-hydroxypropanesulfonate, is the adopted name of the Cosmetic, Toiletry and Fragrance Association (CFTA) for the zwitterion (inner salt) conforming to the formula:

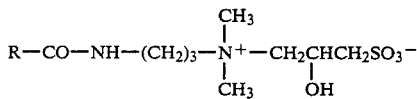

(I)

wherein R—CO— represents the coconut acid radical. It is an amphoteric surfactant recommended for use in cosmetics and toiletries including, among others, as a base in hair conditioning shampoos. For example, in the April, 1980 product information bulletin supplied by Lonza Inc. of Fair Lawn, N.J. on its trademark brand of cocamidopropyl hydroxysultaine, "Lonzaine CS", the specific use of this component in conditioning shampoos is described and exemplified. Similar application in conditioning shampoos is also described and exemplified by the Miranol Chemical Company, Inc. of Irvington, N.J. in the product information bulletin on its trademark brand of cocamido-propyl hydroxysultaine, "Mirataine CBS".

The present invention resides in improved compositions useful for shampooing, cleaning and conditioning hair, preferably for oily hair, which contain, in addition to said cocamidopropyl hydroxysultaine, a quaternary halide salt of an N,N,N-trialkylaminoalkylene gluconamide.

SUMMARY OF THE INVENTION

The term "hair conditioning" is generally accepted to mean "depositing onto the hair surface or into hair fiber certain functional components resistant to water rinse off" (from Shampoo Documentary/Formulary by E. Tolaxesi and A. Bresak, Cosmetics and Toiletries, 96: July, 1981, p. 57.)

The present invention relates to improved hair conditioning shampoos which not only clean and shampoo but, upon rinsing, deposit certain components on the hair surface which impart very desirable properties to the hair, such as body and curl retention, combability, reduction of static (i.e., "flyaway"), increase in luster and shine, smoothness and the like, and reduced sebum spreading. Said components are the aforementioned cocamidopropyl hydroxysultaine and quaternary halide salt of an N,N,N-trialkylaminoalkylene gluconamide.

DETAILED DESCRIPTION OF THE INVENTION

It has now been found that improved hair conditioning shampoo compositions containing the amphoteric surfactant, cocamidopropyl hydroxysultaine, are obtainable by incorporating into such compositions a quaternary halide of an N,N,N-trialkylaminoalklyene gluconamide having the formula:

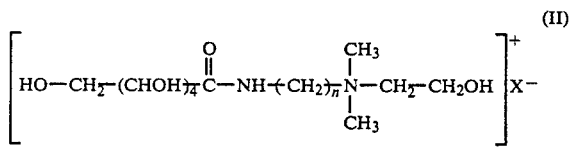

(II)

wherein X is chloro or bromo and n is an integer of from 2 to 4, and preferably 3, of which the quaternary chloride salt having the following formula is most preferred.

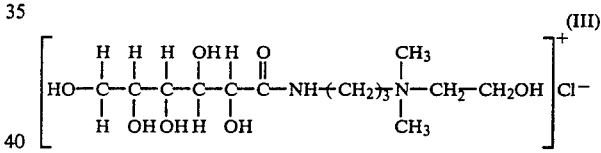

(III)

The preferred quaternary chloride salt of formula (III), chemically known as α-gluconamidopropyl dimethyl-2-hydroxyethyl ammonium chloride (CTFA name: Quaternium 22), is commercially available as a free-flowing 60% aqueous solution (i.e., 60% actives) marketed by the Van Dyk Company, Inc. of Belleville, N.J., under the trademark "Ceraphyl 60".

The newly discovered use of said quaternary halides of the formulas (II) and (III) in topical formulations for the purpose of reducing the spreadability of sebum on the surface of human skin is claimed in application Ser. No. 432,621, entitled "Reducing Sebum Spreading", filed on Oct. 4, 1982, by Morris S. Herstein and Walter P. Smith, two of the co-inventors herein identified.

Sebum, or "skin oil" is produced by the sebaceous glands of the skin, including the scalp, and it migrates to the hair by capillary action. After shampooing, the surface of the hair is devoid of sebum. The hair surface becomes "oily" as sebum migrates along the hair shaft. By reducing or slowing down sebum migration, for example, by adding materials providing such action to the shampoo which then deposit on the hair surface after rinsing, the hair surface stays less oily for a longer period. Said quaternary halide salts of formula (II), and preferably of formula (III), provide such action.

As noted previously, the use of cocamidopropyl hydroxysultaine (I) in hair conditioning shampoos is known. The sultaine is commercially available in the form of a free-flowing 50% aqueous solution (i.e., 50% actives) under such brand names as "Lonzaine ® CS" (marketed by Lonza, Inc.) and "Mirataine ® CBS" (marketed by Miranol Chemical Company, Inc.).

It has now been found that the combined use of the aforementioned cocamidopropyl hydroxysultaine (I) and quaternary halide (II) in an aqueous hair conditioning shampoo composition provides for an increased deposition of said conditioning components on the surface of hair shampooed therewith which results in a substantial increase of desirable hair conditioning properties. Moreover, it does so without a concomitant substantial loss of activity in reducing the spreadability of sebum. These improved features are exemplified from the recorded test data in the following Table 1 by the indicated compositions.

| Acidic Base shampoo Formulation (pH 5.5) | |
|---|---|
| Ingredients | % w/w |
| Sodium lauryl ether sulfate (30%) | 30.0 |
| Citric acid (anhydrous) | 0.4 |
| Water | 69.6 |
| | 100.0 |

TABLE 1

| Base Shampoo Containing % w/w of: | | | | |
|---|---|---|---|---|
| Mirataine CBS | Lonzaine CS | Ceraphyl 60 | Conditioner Deposition[1] | % Reduction in Sebum Spreading[2] |
| — | — | — | 0 | 3 |
| 1 | — | — | 7½ | 26 |
| 10 | — | — | 9 | 21 |
| — | 1 | — | 8 | 16 |
| — | 10 | — | 8½ | 16 |
| — | — | 1 | 9 | 60 |
| — | — | 10 | 10 | 57 |
| 1 | — | 1 | 12 | 41 |
| 4 | — | 1 | 14 | 57 |
| 7 | — | 1 | 13 | 51 |
| 10 | — | 1 | 16 | 45 |
| 4 | — | 2 | 17 | 40 |
| — | 4 | 1 | 15 | 48 |
| 7 | — | 2 | 14 | 39 |
| — | 10 | 1 | 17 | 34 |
| 10 | — | 2 | 18 | 37 |

[1]Absorbance at 520 nm × 10⁻²; see Testing Protocol A.
[2]See testing Protocol B.

The foregoing results, indicating high deposition of conditioning components and high reduction in sebum spreadability for the combined use of the sultaine (I) and quaternary chloride (III), are indeed surprising when contrasted with the results obtained from the same type of base shampoo formulations, except that the cocamidopropyl hydroxysultaine (I) is substituted with related cocamidopropyl betaine (CTFA adopted name) having the formula:

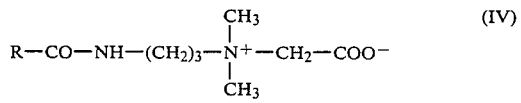

wherein R—CO— represents, as before, the coconut acid radical.

Said betaine (IV) is also an amphoteric surfactant having hair conditioning properties. It is commercially available in the form of a 30% aqueous solution (i.e., 30% actives) under such brand names as "Lonzaine ® C" (marketed by Lonaz, Inc.) and "Monateric ® CAB" (marketed by Mona Industries, Inc.). Substitution of the sultaine (I) with the betaine (IV) has practically no effect on the amount of conditioner deposition and, moreover, there is evidenced a concomitant substantial loss of activity in reducing the spreadibility of sebum. This is exemplified in the following Table 2 with the indicated compositions.

TABLE 2

| Base Shampoo Containing % w/w of: | | | | |
|---|---|---|---|---|
| Lonzaine C | Monoteric CAB | Ceraphyl 60 | Conditioner Deposition | % Reduction in Sebum |
| — | — | — | 0 | 3 |
| 1 | — | — | 8 | 16 |
| 10 | — | — | 8½ | 19 |
| — | 1 | — | 8 | 16 |
| — | 10 | — | 9 | 19 |
| — | — | 1 | 9 | 60 |
| — | — | 10 | 10 | 57 |
| 4 | — | 1 | 7 | 13 |
| 10 | — | 1 | 8 | 16 |
| — | 4 | 1 | 8½ | 13 |
| — | 10 | 1 | 8 | 16 |

A comparison in the data in Table 2 reveals that the percent reduction in the spreadability of sebum by the quaternary chloride of formula (III), when used alone in the base shampoo is about 57–60% and, in contrast, when added to the base shampoo containing the betaine (IV), such percentage is markedly reduced to about 13–16%, i.e., to about one-quarter of the previous value. The data also reveals the absence of any effect on the amount of conditioner deposition resulting from the combined use of (III) and (IV).

Similar results are obtained when an equal amount of sodium or ammonium lauryl sulfate is substituted for the sodium lauryl ether sulfate of the base shampoo.

The procedure utilized in testing for deposition of conditioner components is as follows:

TESTING PROCEDURE A

Materials Required 1. 5% Rubine's Dye (Pyrazol Fast Bordeaux) in water, pH 3.5 (adjusted with HCl).
2. 0.1N NaOH in 1:1 w/w abs. EtOH:water.

Protocol

From 2 to 4 mg/cm² of the material to be tested is gently rubbed on to the volar forearm for 1 minute and then rinsed with cool tap water for 15 seconds and allowed to air dry. After drying, a 1 cm diameter glass cylinder is placed on the treated site and 1 ml of Rubine's Dye is pipetted into the cylinder. After 1 minute, the cylinder and dye are removed and the arm is rinsed under cool tap water for 15 seconds. The remaining dye on the arm is extracted by placing the glass cylinder at the same site and adding 1 ml of the 0.1N NaOH ethanolic solution. The extraction step, which is assisted by rubbing with a teflon rod ("policeman") for 1 minute, is repeated. The combined 2 × 1 ml extractions are diluted to 3.5 ml with the 0.1N NaOH ethanolic solution and read at 520 nm in a colorimeter (e.g., Bausch & Lomb, Spectronic 20 model). The reading obtained is the absorbance of the sample, using a 1 cm path length cuvette. Increased absorbance evidences increased binding of dye to the skin. Since the dye binds to the cationic conditioners at a fixed ratio, an increase in absorbance reflects a corresponding increase in the amount of conditioner deposited, which amount can be readily determined.

The procedure utilized in testing for reduction in sebum spreadability is as follows:

TESTING PROCEDURE B

From 2 to 4 mg/cm$^2$ of the material to be tested is placed on the back of the hand and spread evenly covering a circular area of about 2 inches in diameter. After application of the testing material, a period of one hour is allowed at room temperature for equilibration. After this hour, a 4 μl drop, measured from a micropipette of artificial sebum supplemented with 13% by weight of squalane is deposited substantially in the center of the treated area. The formulation for artificial sebum is

| Ingredients | % w/w |
| --- | --- |
| Squalene | 18.0 |
| Corn Oil | 7.0 |
| 1:1 Mix of Glyceryl Dioleate:Oleic Acid | 1.0 |
| Oleic Acid | 27.0 |
| Ceraphyl 140 (Decyl Oleate) | 43.5 |
| Cholesterol Palmitate | 1.0 |
| Cholesterol | 2.5 |
| | 100.0 |

After a spreading period of 10 minutes, a 1 cm diameter glass cylinder is placed over the center and the sebum within the confines of the cylinder is extracted. The extraction is performed by pipetting 2×0.5 ml aliquots of hexane into the glass cylinder for 30 seconds without agitation. Both hexane extracts are each pipetted into a test tube and evaporated to dryness by a nitrogen gas evaporator. The residue is resolubilized with 0.1 ml hexane and 10 μl of tetracosane is added to the sample as an internal standard. The amount of sebum within the glass cylinder is precisely determined by gas-liquid chromatography (GLC) via determination of the amount of squalane contained in the extract. From this data, the area covered by the spreading of the artificial sebum is calculated. The greater the amount of squalane recovered from the extract, the greater the reduction in sebum spreading.

From the foregoing, it is evident that hair conditioning properties of shampoo compositions containing cocamidopropyl hydroxysultaine (I) are unexpectedly and surprisingly enhanced and improved by the addition of a quaternary halide (II), preferably the chloride (III). This invention thus provides improved hair conditioning shampoo compositions comprising said components. For purposes of this invention, such compositions generally contain from about 0.5 to about 10 percent by weight, based on the total weight of the composition, of said cocamidopropyl hydroxysultaine and, preferably, from about 0.5 to about 5 percent weight; and generally from about 0.1 to about 6 percent by weight of said quaternary halide and, preferably, from about 0.6 to about 3 percent by weight.

Any conventional aqueous hair shampoo formulation can be used as the shampoo base of the subject compositions. Such formulations are well kown in the art and are not discussed in detail herein. The particular type of hair conditioning shampoo composition, which may include gels, creams, lotions, solutions, emulsions and the like just to name a few, is not critical. Such types of compositions are readily prepared by skilled cosmetic chemical formulators. The components (I) and (II) are non-toxic to human skin, are compatible with hydrophilic adjuvants and can be readily incorporated into such compositions. Although said components are utilizable over a wide pH range, best results for purposes of this invention are found when used in acidic hair conditioning shampoos, for example, from about pH 3 to about 6.8 and, preferably, from about pH 5.5 to about 6.8.

Additional aqueous hair conditioning shampoo compositions of this invention are exemplified below showing the improved reduction in sebum spreading derived therefrom.

| Shampoo A (pH 6.0–6.5) | |
| --- | --- |
| Components | % w/w |
| a. Mirataine CBS | 4.0 |
| b. Ceraphyl 60 | 1.0 |
| c. Sodium lauryl sulfate | 30.0 |
| d. Lauramide diethanolamine | 5.0 |
| e. 3,5,7-Triaza-1-azoniotricyclodecane chloride ("Dowicil 200", Dow Chemical Co., Midland, Michigan) | 0.3 |
| f. Ethyl dihydroxypropyl p-aminobenzoic acid/propylene glycol ("Amerscreen P80/20", Amerchol Unit of CPC International, Inc., Madison, New Jersey) | 0.2 |
| g. Water, q.s. to 100.0%. | |
| % Reduction in sebum spreading: | 45% |
| % Reduction in sebum spreading less Component b: | 17% |
| % Reduction in sebum spreading less Components a & b: | 7% |

| Shampoo B (pH 6.0–6.5) | |
| --- | --- |
| Components | % w/w |
| a. Mirataine CBS | 7.0 |
| b. Ceraphyl 60 | 1.0 |
| c. Triethanolamine lauryl sulfate | 37.5 |
| d. Sodium lauryl sarcosinate | 7.0 |
| e. Hydrolyzed keratin polypeptides ("Crotein WKP", Croda Inc., N.Y., N.Y.) | 0.5 |
| f. dl-Panthenol (cosmetic grade) | 1.0 |
| g. Steartrimonium hydrolyzed animal protein ("Crotein Q", Croda Inc., N.Y., N.Y.) | 0.5 |
| h. Lauramide diethanolamine | 3.5 |
| i. Propylene glycol | 1.0 |
| j. Ethyl dihydroxypropyl para-aminobenzoic acid/propylene glycol (Amscreen P80/20) | 0.2 |
| k. Methylparaben | 0.3 |
| l. Citric acid | 0.35 |
| m. Dowicil 200 | 0.3 |
| n. N,N—Dimethyl-N—2-propenyl-1-ammonium chloride, polymer with 2-propenamide ("Merquat 550", Merck & Co., Inc., Rahway, N.J.) | 2.0 |
| o. Sodium chloride | 1.0 |
| p. Odorant | 1.0 |
| q. Water, q.s. ad 100%. | |
| % Reduction in sebum spreading: | 47% |
| % Reduction in sebum spreading less Component b: | 18% |
| % Reduction in sebum spreading less Components a & b: | 10% |

It will be understood by those having skill in the art that the invention is not limited to the specific examples which have been offered as particular embodiments and that modifications can be made without departing from the spirit thereof.

We claim:

1. An aqueous hair conditioning shampoo composition containing, percentages given being by weight based upon the total weight of the composition, from about 0.5 percent to about 10 percent of cocamidopropyl hydroxysultaine and from about 0.1 to about 6 percent of a quaternary halide of an N,N,N-trialkylaminoalkylene gluconamide having the formula:

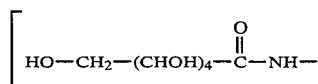

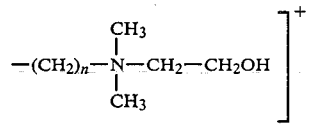

wherein X is chloro or bromo and n is an integer of from 2 to 4.

2. The composition of claim 1 wherein said n is the integer 3.

3. An aqueous hair conditioning shampoo composition containing, percentages given being by weight based upon the total weight of the composition, from about 0.5 to about 10 percent of cocamidopropyl hydroxysultaine and from about 0.1 to about 6 percent of a quaternary chloride of an N,N,N-trialkylaminoalkylene glyconamide having the formula:

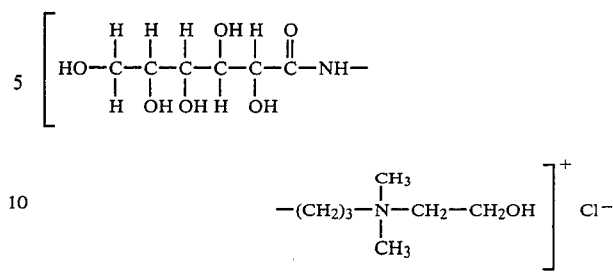

4. An aqueous hair conditioning shampoo composition containing, percentages given being by weight based upon the total weight of the composition, from about 0.5 to about 5 percent of cocamidopropyl hydroxysultaine and from about 0.6 to about 3 percent of a chloride of an N,N,N-trialkylaminoalkylene gluconamide having the formula:

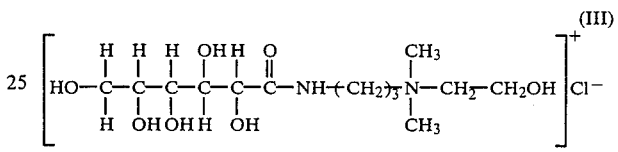

5. The composition of claim 4 wherein the pH is from about 3 to about 6.8.

6. The composition of claim 4 wherein the pH is from about 5.5 to about 6.8.

* * * * *